United States Patent [19]

Kato et al.

[11] Patent Number: 5,258,129
[45] Date of Patent: Nov. 2, 1993

[54] FLUID-PERMEABLE AGENT FOR NON-WOVEN SHEETS OF POLYOLEFIN FIBERS AND METHOD OF APPLICATION THEREOF

[75] Inventors: Tomohiro Kato; Yoshio Takasu; Makoto Minafuji, all of Aichi, Japan

[73] Assignee: Takemoto Yushi Kabushiki Kaisha, Japan

[21] Appl. No.: 782,871

[22] Filed: Oct. 15, 1991

Related U.S. Application Data

[63] Continuation-in-part of Ser. No. 403,037, Aug. 31, 1989, abandoned, which is a continuation-in-part of Ser. No. 272,650, Nov. 17, 1988, abandoned.

[30] Foreign Application Priority Data

Dec. 2, 1987 [JP] Japan ................ 62-305325

[51] Int. Cl.$^5$ .......................................... D06M 15/647
[52] U.S. Cl. ........................................ 252/8.9; 252/8.6; 252/8.8; 528/29; 8/DIG. 1; 524/262; 524/265; 524/581
[58] Field of Search ............. 252/8.8, 8.9; 528/29; 8/DIG. 1; 524/262, 265, 581

[56] References Cited

U.S. PATENT DOCUMENTS 4,535,113 8/1985 Foster et al. .................. 524/262

FOREIGN PATENT DOCUMENTS 1-006176 1/1989 Japan .

Primary Examiner—Ellen M. McAvoy
Attorney, Agent, or Firm—Heller, Ehrman, White & McAuliffe

[57] ABSTRACT

A fluid-permeable agent for providing fluid-permeability to non-woven sheets of polyolefin fibers contains 50 wt % or more of polyoxyalkylene modified silicone shown by Formula (A) given below:

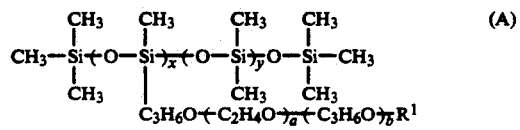

where x is an integer in the range of 1-10, y is an integer in the range of 7-100, a is an integer equal to or greater than 5, b is an integer equal to or less than 95, (a+b) is an integer equal to or less than 100 and $R^1$ is H or alkyl group with 1-12 carbon atoms. The agent may additionally contain surfactants of certain specified kinds and is applied at a rate of 0.1-0.5 wt % with respect to the fibers for good results.

9 Claims, No Drawings

FLUID-PERMEABLE AGENT FOR NON-WOVEN SHEETS OF POLYOLEFIN FIBERS AND METHOD OF APPLICATION THEREOF

This is a continuation-in-part of application Ser. No. 07/403,037 filed Aug. 31, 1989, now abandoned, which is a continuation-in-part of application Ser. No. 07/272,650 filed Nov. 17, 1988, now abandoned.

BACKGROUND OF THE INVENTION

This invention relates to fluid-permeable agents for non-woven sheets made of polyolefin fibers such as composite synthetic fibers having sheath-core structure made of two or more polymers with different melting points having polyolefin polymer sheaths and also to application methods of such agents. More particularly, this invention relates to agents to be applied to such fibers for providing durability and fluid-permeability and also to methods of applying such agents.

Recently, non-woven sheets by a dry-bonding process and more particularly bondable non-woven sheets are coming to be frequently used in medical supplies and hygienical articles. For diapers, napkins and the like, polyolefin fibers and composite polyethylene fibers are frequently used in view of their skin-comfortability (that is, softness and absence of discomfort from wetting). In order to improve product characteristics such as bulkiness, restorability and shape-stability against heat, on the other hand, use is frequently made of heat-bondable composite fibers comprised of polyester fibers and polypropylene fibers as the core and polyolefin polymers as the sheath.

In order to eliminate user's discomfort from a diaper, a napkin and the like caused by sweat, urine, menstrual fluid and other body fluids, it is considered important not only that the body-facing parts of these products be wettable but also their wettability can be quickly manifested. For this reason, fluid-permeability within a short time is a required characteristic of polyolefin fibers of which these body-facing parts are comprised. Since diapers, in particular, are generally worn by infants, seniors and very sick persons who cannot take care of themselves, a single diaper should be able to handle two or more discharges without causing discomfort to the wearer. For this reason, durability of fluid-permeability (or durability against repeated use) is another strongly required characteristic.

Prior art methods of providing fluid-permeability to polyolefin fibers and sheaths of polyolefin composite fibers include (1) application of a low-molecular weight hydrophilic compound, (U.S. Pat. Nos. 3664,343 and 3,821,021 and U.S. patent application Ser. No. 210,636 filed Jun. 23, 1988, now abandoned assigned to the present assignee) (2) application of a hydrophilic macromolecular resin, (U.S. Pat. Nos. 3,934,587, 4,297,410, 4,406,660 and 4,718,899) (3) improvement of surface characteristics by chemical processing, solvent processing, plasma processing, corona discharge processing, etc. By the first of the above methods, however, not only desired fluid-permeability cannot be obtained because these agents cannot wet the fiber surface satisfactorily but also there is no durability even if fluid-permeability can be obtained to a certain extent and, in many instances, the user's skin is seriously irritated. The second of the above methods, on the other hand, generally cannot provide sufficient fluid-permeability. Additional disadvantages include insufficiency in durability if use is made of an agent which can provide fluid-permeability to a certain extent. Moreover, agents of this type have the tendency of causing troubles of various kinds during the production process of non-woven sheets. As for the third of the above methods, although it provides relatively favorable results regarding skin-irritation and permeability, resultant fluid-permeability tends to deteriorate with time along with the polar groups which are generated by the surface changes of the fibers. In other words, this method not only provides insufficient durability but also is itself uneconomical.

There have been proposals, on the other hand, to use a hydrophilic polymer as base material and to partially coat its surface with a hydrophobic compound. A water repellant polymer may be used as the hydrophobic compound as disclosed in U.S. Pat. No. 3,934,587. Alternatively, us may be made of a compound of silicon or fluorine as disclosed in U.S. Pat. No. 3,838,692. These proposed methods are equally unsatisfactory because a basically hydrophilic polymer is used as the base material and the aforementioned characteristics of basically hydrophobic polyolefin fibers are lacking.

SUMMARY OF THE INVENTION

Polyolefin fibers being basically very poor in permeability because of their low surface energy characteristics, it is an object of the present invention to provide fluid-permeable agents for non-woven sheets of polyolefin fibers with which the aforementioned problems of prior art agents can be eliminated.

The present invention has been completed by the present inventors as a result of their diligent studies in view of the aforementioned and other objects and is based on their discovery that desired results are obtainable by agents containing more than a specified amount f specified kinds of polyoxyalkylene modified silicone and also a specified kind of surfactant appropriately selected for the purpose.

DETAILED DESCRIPTION OF THE INVENTION

Fluid-permeable agents according to the present invention for non-woven sheets of polyolefin fibers are characterized as containing (a) 50–100 wt % of polyoxyalkylene modified silicone shown by the following Formula A:

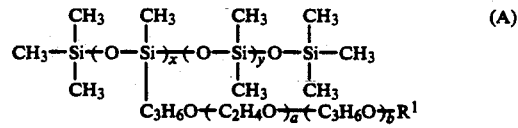

where x is an integer in the range of 1–10, y is an integer in the range of 7–100, a is a non-zero integer equal to or greater than 5, b is an integer equal to or less than 95, (a+b) is an integer equal to or less than 100 and $R^1$ is H or alkyl group with 1–12 carbon atoms and (b) 0–45 wt % of surfactants of certain kinds to be specified below. As for polyoxyalkylene modified silicone shown by Formula (A), it may be obtained, for example, by hydrosililation reaction of Compound (i) and Compound (ii), Compound (i) being end ($\omega$-position) alkylated polyalkylene glycol ether of allyl alcohol or polyalkylene glycol ether monoallyl ether and Compound (ii) being methyl hydrogen polysiloxane with random or block positioned hydrogen atoms shown by the formula

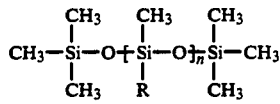

where Rs and random or block positioned mixture of $CH_3$ and H and n is $x+y$ (and hence 8-110). An example of such hydrosililation reaction is shown below:

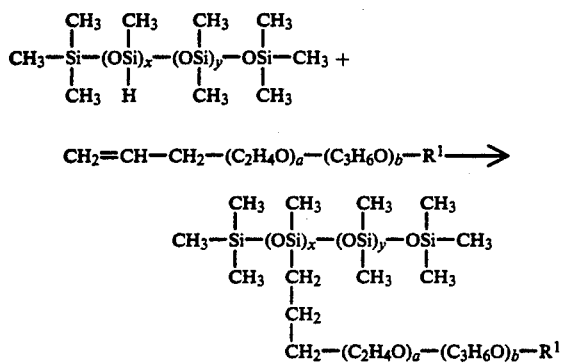

Polyoxyalkylene modified silicones of the present invention are characterized by their small water solubility because of their structure. Their solubility is such that they can be emulsified barely with the help of an emulsifier. In fact, the integer x in Formula (A) must be or greater in order to obtain satisfactory fluid-permeability by providing a minimum of water solubility to the obtained modified silicone, but if x is greater than 10, on the other hand, water solubility of the obtained modified silicone becomes too large and, although its fluid-permeability may be satisfactory, its durability becomes insufficient. Similarly, the integer a in Formula (A) must be 5 or greater in order to obtain satisfactory fluid-permeability by providing a minimum of water solubility to the obtained modified silicone, but if $(a+b)$ is greater than 100, durability of the obtained modified silicone, in particular, is significantly affected. In this regard, the molar ratio and the weight ratio of the polyoxyethylene part indicated together by a and the polyoxypropylene part indicated together by b is also influential and the ratio $(a \times 44)/(b \times 58)$ should preferably be greater than 25/75. If $R^1$ in Formula (A) is an alkyl group with more than 12 carbon atoms, furthermore, fluid-permeability of the obtained modified silicone is insufficient. If the integer y in Formula (A) is smaller than 7, durability of the obtained modified silicone is poor and if it is greater than 100, on the other hand, fluid-permeability is adversely affected. Agents according to the present invention contain polyoxyalkylene modified silicone of the kind described above by more than 50 wt %. If the content is less than 55 wt %, sufficient fluid permeability and durability cannot be obtained.

It is preferable to use polyoxyalkylene modified silicone together with a surfactant of specified kinds in order to improve the characteristics related to the production processes of non-woven sheets without adversely affecting the aforementioned polyoxyalkylene modified silicones. Among preferable surfactants are non-ionic surfactants derived from an addition reaction of alkylene oxide such as ethylene oxide and propylene oxide to an active hydrogen compound having alkyl or alkenyl group with 11-22 carbon atoms as hydrophobic groups, 3-10 moles of the alkylene oxide being added per hydrophobic group of the active hydrogen compound in the addition reaction. Such a surfactant is added to an agent at the concentration of about less than 45 wt %. With a non-ionic surfactant having alkyl or alkenyl group with less than 11 carbon atoms, the agent is not uniformly attached to fibers and both its fluid-permeability and durability become poor. The result is approximately the same if the number of carbon atoms exceeds 22. If less than 3 moles of alkylene oxide is added, both solubility into water and stability of solution become poor and abnormal attachment to fibers may occur such that fluid-permeability becomes poorer. If more than 10 moles of alkylene oxide is added, on the other hand, durability of polyoxyalkylene modified silicone is adversely affected.

Examples of preferable non-ionic surfactant include POE(7) stearyl ether, POE(5) oleate ether, PEG(400) stearate, POE(10) lauryl ether stearate, POE(4) cetyl amino ether, POE(7) stearoyl amino ether, ethylene oxide (7 mole) adduct of sorbitan monostearate, trimethylol propane-ethylene oxide (9 mole) adduct of tristearate, ethylene oxide (10 mole) adduct of pentaerythritol distearate, castor oil ethylene oxide (25 moles) adduct of trioleate, and propylene oxide (4 mole) ethylene oxide (6 mole) adduct of stearyl alcohol. In the above and hereinafter, POE and PEG respectively indicate polyoxyethylene and polyethyleneglycol and the numeral inside the parentheses which follow indicates the molar number of addition.

Preferable surfactants of another kind to be used together with the aforementioned polyoxyalkylene modified silicones according to the present invention include alkyl phosphate salts shown by the following general formula (Formula (B)), quaternary ammonium salts shown by the following general formula (Formula (C)) and alkyl imidazolinium salts shown by the following general formula (Formula (D)):

where $R^1$ is alkyl or alkenyl group with 12-18 carbon atoms, M is Na, K or ammonium, and a and b are integers equal to or greater than 1 such that $a+b = 3$;

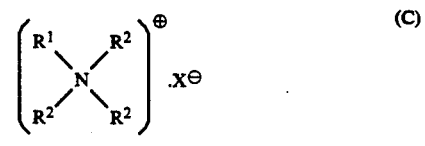

and

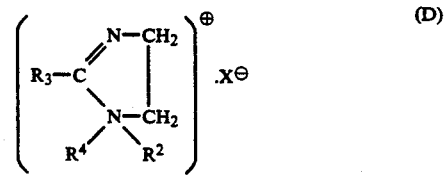

where $R^1$ is alkyl or alkenyl group with 12-18 carbon atoms, $R^2$ is H, alkyl or hydroxyalkyl group with 1-2 carbon atoms or $R^1$, $R^3$ is alkyl or alkenyl group with 11-17 carbon atoms, $R^4$ is $C_2H_4OH$, $C_2H_4NH_2$, $C_2H_4NHCOCH_3$ or $C_2H_4NHCOR^3$, and X is halogen, residue of organic or inorganic acid or alkyl sulfate or alkyl phosphate with 1-2 carbon atoms. It is preferable that these surfactants be contained by 5-45 wt % in the agent of the present invention.

When such (alkyl phosphate, quaternary ammonium and alkyl imidazolinium) salts are used together with the aforementioned polyoxyalkylene modified silicones and non-ionic surfactants of the present invention, it is preferable to mix them together such that the mixture has 55-70 wt % of polyoxyalkylene modified silicone, 20-35 wt % of non-ionic surfactant and 10-20 wt % of one selected from the group consisting of alkyl phosphate salts, quaternary ammonium salts and alkyl imidazolinium salts. The salts of the aforementioned group are capable of improving the processability of non-woven sheets during their production without adversely affecting the fluid-permeability and durability of polyoxyalkylene modified silicones. In particular, antistatic characteristics, card-processability and uniformity of web during a web-formation process can be obtained with them. The limiting conditions presented above with respect to these salts are important, for example, in that those with smaller alkyl or alkenyl groups than specified above adversely affect the durability of polyoxyalkylene modified silicones and that those with larger alkyl or alkenyl groups than specified above tend to obstruct the fluid-permeability of polyoxyalkylene modified silicones. Examples of ammonium in Formula (B) include $NH_4$, $NH(CH_3)_3$, $NH(C_2H_5)_3$, $NH_2(CH_2CH_2OH)_2$ and $NH(CH_2CH_2OH)_3$.

Composite fibers with a sheath part of polyethylene polymer and a core part of polypropylene or polyester fibers are representative examples of polyolefin fibers to which the fluid-permeable agents of the present invention are applicable but the present invention is by no means limited to application to such fibers. The agents of the present invention are also applicable not only to composite fibers in general with a sheath part of polyolefin polymer and a core part of another polymer with a different melting point but also to polyethylene fibers, polypropylene fibers and other copolymer fibers not by composite spinning.

The agents of the present invention should preferably be applied to such polyolefin fibers generally at the rate (with respect to the fibers) of 0.05-0.7wt % and more preferably 0.1-0.5wt %. Methods of application include dipping, spraying and the roller-touch method. The polyolefin fibers to which an agent has been applied is dried for production of non-woven sheets by card processing and heat bonding.

In what follows, examples of tests and their results are presented to further describe the present invention but it goes without saying that these examples are not intended to limit the scope of the invention. For testing, agents inclusive of thirteen test examples and five comparison examples were prepared with constituents selected as shown in Table 1. Samples each with 0.2wt % of one of these agents were prepared by dipping composite fibers of 2 denier ×51 mm cut length with sheath part of polyethylene and core part of polyester in 1.0% solution of each of the agents listed in Table 1 for two minutes at 40° C., thereafter squeezing to 20wt % and wind-drying for 60 minutes at 60° C.

Antistatic characteristics of the samples were evaluated by keeping them for 24 hours under temperature-humidity conditions of 25 C and 40%RH and measuring the generated voltage as they were passed through an opener and a roller card under these conditions such that the web weight became 24g/m².

TABLE 1

| Classification | Component | Content (wt %) |
|---|---|---|
| Example 2 | Silicone of Formula (A) with x = 2, y = 20, a = 45, b = 36, $R^1$ = H | 100 |
| Example 3 | Silicone of Formula (A) with x = 6, y = 52, a = 14, b = 25, $R^1$ = H | 100 |
| Example 6 | Silicone of Example 2 | 95 |
|  | Potassium stearyl phosphate | 15 |
| Example 9 | Silicone of Example 2 | 70 |
|  | Stearic acid PEG-400 monostearate (*) | 20 |
|  | Potassium stearyl phosphate | 10 |
| Example 10 | Silicone of Example 3 | 60 |
|  | Sorbitan monopalmitate | 25 |
|  | Potassium laurel phosphate | 15 |
| Comparison 1 | Sorbitan monostearate | 30 |
|  | Ethylene oxide 10 mole adduct of stearic amide | 20 |
|  | Potassium cetyl phosphate | 50 |
| Comparison 2 | Silicone of Formula (A) with x = 0, y = 18 (dimethyl silicone) | 80 |
|  | Potassium cetyl phosphate | 20 |
| Comparison 3 | Silicone of Formula (A) with x = 1, y = 20, a = 3, b = 30, $R^1$ = H | 100 |
| Comparison 4 | Silicone of Example 1 | 40 |
|  | Ethylene oxide 7 mole adduct of stearic amide | 30 |
|  | Potassium cetyl phosphate | 30 |
| Comparison 5 | Silicone of Example 4 | 35 |
|  | Ethylene oxide 10 mole adduct of stearic amide | 35 |
|  | Glycerine sesquistearate | 30 |

(*) PEG-400: Polyethylene glycol with molecular weight of 400

TABLE 2

|  | Voltage Generated (kV) | Permeability (sec) | Durability Permeability After Each Use (sec) | | | Total Number of Repetitions |
|---|---|---|---|---|---|---|
|  |  |  | Once | Twice | Thrice |  |
| Example |  |  |  |  |  |  |
| 1 | −0.3 | 7 | 11 | 10 | 12 | 9 |
| 2 | 0.3 | 10 | 12 | 15 | 25 | 6 |
| 3 | −0.5 | 5 | 6 | 18 | 29 | 5 |
| 4 | −0.3 | 3 | 5 | 7 | 8 | 11 |
| 5 | −0.5 | 10 | 12 | 14 | 18 | 8 |
| 6 | −0.5 | 6 | 18 | 29 | 43 | 5 |
| 7 | ±0.0 | 4 | 3 | 16 | 27 | 7 |
| 8 | −0.5 | 3 | 5 | 11 | 13 | 9 |
| 9 | −0.1 | 2 | 7 | 21 | 35 | 6 |
| 10 | ±0.0 | 2 | 6 | 14 | 20 | 7 |

TABLE 2-continued

| | Voltage Generated (kV) | Permeability (sec) | Durability Permeability After Each Use (sec) | | | Total Number of Repetitions |
|---|---|---|---|---|---|---|
| | | | Once | Twice | Thrice | |
| 11 | −0.4 | 2 | 9 | 17 | 22 | 12 |
| 12 | ±0.0 | 7 | 14 | 17 | 19 | 13 |
| 13 | −0.5 | 4 | 12 | 15 | 19 | 12 |
| Comparison | | | | | | |
| 1 | −0.8 | 60≦ | — | — | — | 0 |
| 2 | −0.8 | 60≦ | — | — | — | 0 |
| 3 | −2.3 | 54 | 60≦ | — | — | 0 |
| 4 | −0.5 | 26 | 44 | 60≦ | — | 1 |
| 5 | −1.2 | 32 | 41 | 50 | 60≦ | 2 |

For evaluation of fluid-permeability, non-woven sheet samples were prepared by cutting the aforementioned card web to 10 cm×10 cm and thermally testing for 30 seconds by a heater plate of 130° C. After these sheet samples were conditioned for 24 hours within a chamber at 20.C and 60%RH, they were placed on a horizontal plate, water drops of 0.4ml were dropped from a height of 10mm and the time required for each water drop to be completely absorbed was measured. For evaluating durability, after 80ml of ion exchange water was sprayed over the sample to be passed therethrough, the samples were wind-dried for 90 minutes at 40° C. and the evaluation of fluid-permeability was repeated. If the measured time was 60 seconds or less, it was recorded and the process described above was repeated. The total number of repetitions was also recorded.

Table 2, which summarizes the results of these tests, clearly shows that the agents according to the present invention can provide superior fluid-permeability and durability to non-woven sheets made from polyolefin fibers and improve processability of such non-woven sheets during their production.

What is claimed is:

1. A method of providing fluid-permeability to non-woven sheet of polyolefin fibers, said method comprising the steps of applying a fluid-permeable agent to polyolefin spun fibers at a rate of 0.1–0.5 wt % with respect to said fibers and thereafter using said fibers for production of non-woven sheets, said agent being characterized as containing 0–45 wt % of surfactant and 55–100 wt % of polyoxyalkylene modified silicone shown by Formula (A) given below:

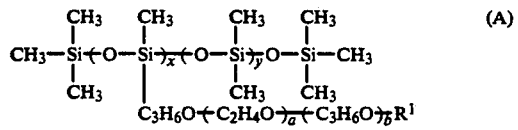

where x is an integer in the range of 1–10, y is an integer in the range of 7–100, a is an integer equal to or greater than 5, b is a non-zero integer equal to or less than 95, (a+b) is an integer equal to or less than 100 and $R^1$ is H or alkyl group with 1–12 carbon atoms.

2. The method of claim 1 wherein said surfactant includes one or more selected from the following:
   (a) non-ionic surfactant derived from an addition reaction of alkylene oxide with 2–3 carbon atoms to active hydrogen compound having alkyl or alkenyl group with 11–22 carbon atoms as hydrophobic group, 3–10moles of alkylene oxide being added per hydrophobic group of said active hydrogen compound in said addition reaction;
   (b) alkyl phosphate salt shown by Formula (B) given below:

where $R^1$ is alkyl or alkenyl group with 12–18 carbon atoms, M is Na, KI or ammonium, and a and b are integers equal to or greater than 1 such that a+b=3;
   (c) quaternary ammonium salt shown by the following formula:

where $R^1$ is alkyl or alkenyl group with 12–18 carbon atoms, $R^2$ is H, alkyl or hydroxyalkyl group with 1–2 carbon atoms or $R^1$, and X is halogen, residue of organic or inorganic acid, or alkyl sulfate or alkyl phosphate with 1–2 carbon atoms; and
   (d) alkyl imidazolinium salt shown by the following formula:

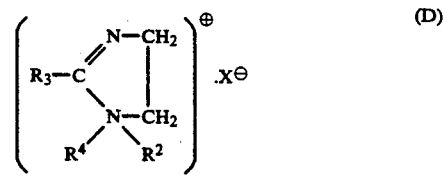

$R^2$ is H, alkyl or hydroxyalkyl group with 1–2 carbon atoms, or alkyl or alkenyl group with 12–18 carbon atoms, X is halogen, residue of organic or inorganic acid, or alkyl sulfate or alkyl phosphate with 1–2 carbon atoms, $R^3$ is alkyl or alkenyl group with 11–17 carbon atoms and $R^4$ is $C_2H_4OH$, $C_2H_4NH_2$, $C_2H_4NHCOCH_3$ or $C_2H_4NHCOR^3$.

3. The method of claim 2 characterized as containing 55–70 wt % of said polyoxyalkylene modified silicone, 20–35 wt % of said non-ionic surfactant and 10–20 wt % of said alkyl phosphate salt.

4. The method of claim 2 characterized as containing 55–70 wt % of said polyoxyalkylene modified silicone, 20–35 wt T of said non-ionic surfactant and 10–20 wt % of said quaternary ammonium salt.

5. The method of claim 2 characterized as containing 55–70 wt % of said polyoxyalkylene modified silicone, 20–35 wt % of said non-ionic surfactant and 10–20 wt % of said alkyl imidazolinium salt.

6. A fluid-permeable agent for providing fluid-permeability to non-woven sheets of polyolefin fibers, said agent being characterized as containing 0–45 wt % of surfactant and 55–100 wt % of polyoxyalkylene modified silicone shown by Formula (A) given below:

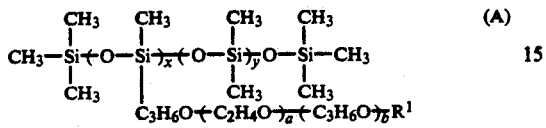

where x is an integer in the range of 1–10, y is an integer in the range of 7–100, a is an integer equal to or greater than 5, b is a non-zero integer equal to or less than 95, (a+b) is an integer equal to or less than 100 and $R^1$ is H or alkyl group with 1–12 carbon atoms, and said surfactant including one or more selected from the following:

(a) non-ionic surfactant derived from an addition reaction of alkylene oxide with 2–3 carbon atoms to active hydrogen compound having alkyl or alkenyl group with 11–22 carbon atoms as hydrophobic group, 3–10 moles of alkylene oxide being added per hydrophobic group of said active hydrogen compound in said addition reaction;

(b) alkyl phosphate salt shown by Formula (B) given below:

where $R^1$ is alkyl or alkenyl group with 12–18 carbon atoms, M is Na, K or ammonium, and a and b are integers equal to or greater than 1 such that a+b=3;

(c) quaternary ammonium salt shown by the following formula:

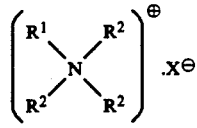

where $R^1$ is alkyl or alkenyl group with 12–18 carbon atoms, $R^2$ is H, alkyl or hydroxyalkyl group with 1–2 carbon atoms or $R^1$, and X is halogen, residue of organic or inorganic acid, or alkyl sulfate or alkyl phosphate with 1–2 carbon atoms; and (d) alkyl imidazolinium salt shown by the following formula:

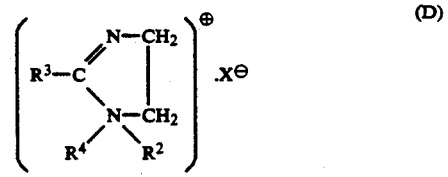

where $R^2$ is H, alkyl or hydroxyalkyl group with 1–2 carbon atoms, or alkyl or alkenyl group with 12–18 carbon atoms, X is halogen, residue of organic or inorganic acid, or alkyl sulfate or alkyl phosphate with 1–2 carbon atoms, $R^3$ is alkyl or alkenyl group with 11–17 carbon atoms and $R^4$ is $C_2H_4OH$, $C_2H_4NH_2$, $C_2H_4NHCOCH_3$ or $C_2H_4NHCOR^3$.

7. The agent of claim 6 characterized as containing 55–70 wt % of said polyoxyalkylene modified silicone, 20–35 wt % of said non-ionic surfactant and 10–20 wt % of said alkyl phosphate salt.

8. The agent of claim 6 characterized as containing 55–70 wt % of said polyoxyalkylene modified silicone, 20–35 wt % of said non-ionic surfactant and 10–20 wt % of said quaternary ammonium salt.

9. The agent of claim 6 characterized as containing 55–70 wt % of said polyoxyalkylene modified silicone, 20–35 wt % of said non-ionic surfactant and 10–20 wt % of said alkyl imidazolinium salt.

* * * * *